US012779159B2

(12) United States Patent
Schwaibold

(10) Patent No.: US 12,779,159 B2
(45) Date of Patent: Nov. 3, 2026

(54) DEVICE AND METHOD FOR DETERMINING THE WEAR OF A VENTILATOR

(71) Applicant: Loewenstein Medical Technology S.A., Luxembourg (LU)

(72) Inventor: Matthias Schwaibold, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1074 days.

(21) Appl. No.: 17/935,285

(22) Filed: Sep. 26, 2022

(65) Prior Publication Data

US 2023/0095821 A1 Mar. 30, 2023

(30) Foreign Application Priority Data

Sep. 27, 2021 (DE) ......................... 102021004853.9
Oct. 1, 2021 (DE) ......................... 102021004932.2

(51) Int. Cl.
*A61M 16/00* (2006.01)
*G05B 23/02* (2006.01)

(52) U.S. Cl.
CPC ...... *A61M 16/022* (2017.08); *A61M 16/0003* (2014.02); *G05B 23/0205* (2013.01)

(58) Field of Classification Search
CPC .............. G16H 40/40; A61M 2205/52; A61M 2205/33; A61M 2205/35
See application file for complete search history.

(56) References Cited

U.S. PATENT DOCUMENTS

2011/0259333 A1* 10/2011 Sanchez ............... G09G 3/3426 345/1.3
2020/0013501 A1* 1/2020 Page ...................... G08B 21/24
2022/0016571 A1* 1/2022 Yehya .................. G05B 13/048
2022/0020488 A1* 1/2022 Kennedy ................ G16H 20/40

FOREIGN PATENT DOCUMENTS

CN 111554385 A * 8/2020 ............. G16H 40/40
CN 111816291 A * 10/2020 ............. G16H 40/40
CN 111931956 A * 11/2020 ............. G16Y 40/40
RU 2690395 C1 * 6/2019 ............. H04W 4/80

OTHER PUBLICATIONS

Umbelino Vanda et al, "Standards about Medical Equipment Maintenance—A Survey", 2019 IEEE 6th Portuguese Meeting on Bioengineering (ENBENG), IEEE, (Feb. 22, 2019), doi:10.1109/ENBENG.2019.8692460, pp. 1-4.

* cited by examiner

*Primary Examiner* — Brandy S Lee
*Assistant Examiner* — Rohan Patel
(74) *Attorney, Agent, or Firm* — Abel Schillinger, LLP

(57) ABSTRACT

Device for determining a usage intensity of a ventilator, having at least one control unit and a usage clock, which is designed and configured to detect the duration of the usage of the ventilator. The device is characterized in that the control unit is configured and designed to offset the duration of the usage of the ventilator with at least one wear factor, in order to determine at least one wear therefrom.

2 Claims, 3 Drawing Sheets

DEVICE AND METHOD FOR DETERMINING THE WEAR OF A VENTILATOR

CROSS-REFERENCE TO RELATED APPLICATIONS

The present application claims priority under 35 U.S.C. § 119 of German Patent Application Nos. 102021004853.9, filed Sep. 27, 2021, the entire disclosure of which is expressly incorporated by reference herein.

BACKGROUND OF THE INVENTION

1. Field of the Invention

The invention relates to a device and a method for determining the wear of a ventilator.

2. Discussion of Background Information

Modern ventilators offer a whole array of different treatment options and functions. Depending on the treatment, the stress which acts on individual parts varies here. For efficient resource utilization, it is helpful to initiate maintenance actions in a timely manner in order to maintain the device before damage.

Ventilators known from the prior art only offer very simple possibilities here for ascertaining intervals in which the device is maintained. In general, solely the usage time alone is recorded and the next maintenance is determined based thereon.

In view of the foregoing, it would be advantageous to have available a device and a method for achieving an increased operation safety of ventilators.

Moreover, malfunction-free ventilation is to be ensured, wherein careful material use is to be achieved at the same time. Costs and resources can thus be saved for material and transport and the environment is additionally protected.

SUMMARY OF THE INVENTION

The invention provides a device for determining a usage intensity of a ventilator, having at least one control unit and a usage clock, which is designed and configured to detect the duration of the usage of the ventilator. The device is characterized in that the control unit is configured and designed to offset the duration of the usage of the ventilator with at least one wear factor, to determine at least one wear therefrom.

The duration of the usage of the ventilator can be determined directly or indirectly here. A direct determination of the duration is carried out, for example, by a clock or a timer. An indirect determination of the duration is carried out, for example, in consideration of the wear of at least one component and/or in consideration of at least one wear factor, wherein in addition the results of a direct determination of the duration can be taken into consideration.

In some embodiments, the device is characterized in that the control unit is configured and designed to determine a plurality of wear factors.

In some embodiments, the device is characterized in that the control unit is configured and designed to offset the wear factors to form an overall factor for the ventilator and to determine an overall wear of the ventilator via an offset of the overall factor with the duration of the usage.

In some embodiments, the device is characterized in that the control unit is configured and designed to determine at least one wear factor in each case for individual components and/or component groups of the ventilator.

In some embodiments, the device is characterized in that the control unit is configured and designed to offset the duration of the usage of the ventilator with the respective wear factors of the components and/or component groups, to determine therefrom a wear of the respective component and/or component group.

In some embodiments, the device is characterized in that the control unit is configured and designed to determine the wear factor from at least one operating parameter of the ventilator, wherein the at least one operating parameter is selected from firmware version; hardware version; treatment mode; treatment pressures; IPAP/EPAP ramp; leakage; speed of the turbine/fan; speed changes of the turbine; braking processes of the turbine; switching processes of valves; trigger settings; respiratory flow; respiratory rate; mask used; hose system used; humidifier; ambient temperature; ambient humidity; number of hygienic preparations; day or night mode; oxygen feed; duration and/or amount of oxygen admixing; use of auxiliary functions such as hose heating and/or respiratory gas humidification; frequency of ventilation maneuvers; use of additional sensors; status and/or source of the power supply; point in time of the last maintenance.

In some embodiments, the device is characterized in that the control unit is configured and designed to determine a wear for at least one component selected from turbine; humidifier; water chamber; air filter; hose; patient interface; sound insulation foams; electronics; power supply unit; accumulator; sensors; measurement cells; valves, which is independent of the overall wear.

In some embodiments, the device is characterized in that the usage clock is configured and designed to also detect a standby time of the ventilator in addition to the duration of the usage of the ventilator.

In some embodiments, the device is characterized in that the control unit is configured and designed to also incorporate the standby time of the ventilator in the overall wear of the ventilator.

In some embodiments, the device is characterized in that the control unit is configured and designed to determine an average wear factor for each wear factor and to make a prediction with respect to the respective wear on the basis of the respective average wear factor.

In some embodiments, the device is characterized in that the control unit is configured and designed to determine the average wear factor from the progression over time of the respectively underlying wear factor, wherein the average wear factor includes a chronological weighting.

In some embodiments, the device is characterized in that the control unit is configured and designed to weight wear factors which are more recent in the progression over time more strongly for the average wear factor.

In some embodiments, the device is characterized in that the control unit is configured and designed to generate a message, which contains at least one notification of a maintenance, on the basis of the determined wear and/or the prediction of the wear.

In some embodiments, the device is characterized in that the control unit is configured and designed to recognize when the maintenance is completed, wherein the message is deleted and the maintenance point in time is saved in the ventilator.

In some embodiments, the device is characterized in that the control unit is configured and designed to determine an optimal maintenance point in time on the basis of the determined wear and/or the prediction of the wear and generate a corresponding message.

In some embodiments, the device is characterized in that the control unit is configured and designed, after a duration after the maintenance point in time is exceeded, to generate an alarm message and if the maintenance still does not occur, to block the ventilator and/or specific functions of the ventilator until the maintenance has been carried out.

In some embodiments, the device is characterized in that the control unit is configured and designed, after completed maintenance, to unblock the blocked ventilator or the blocked functions again and/or to deactivate the alarm message.

In some embodiments, the device is characterized in that the control unit is configured and designed to recognize on the basis of the determined wear whether a component of the ventilator has to be replaced and to generate a replacement message, wherein the replacement message is transmitted at least to a distant remote station and the replacement message triggers an action at the distant remote station, which results in the shipping of a replacement component to a predefined location.

In some embodiments, the device is characterized in that the control unit is configured and designed to generate, together with the replacement message, an item of information about how the component to be replaced is to be exchanged and recognizes automatically when the component to be replaced is replaced by a new component.

In some embodiments, the device is characterized in that the control unit is configured and designed to create a usage report in periodic time intervals, which comprises at least one wear and/or a fee based on the wear.

In some embodiments, the device is characterized in that the control unit is configured and designed to calculate the fee from a base fee and a wear fee, wherein the wear fee is automatically adapted to the wear.

In some embodiments, the device is characterized in that the control unit is configured and designed to use a consumption of data volume as an operating parameter.

In some embodiments, the device is characterized in that the control unit is configured and designed, after the consumption of a specific data volume, to reduce the amount of data transmitted and/or the frequency of the data transfers and/or to deactivate a manual transmission function.

The invention also relates to a method for determining a usage intensity of a ventilator, wherein the time period of the usage of the ventilator is detected. The method is characterized in that the time period of the usage of the ventilator is offset with at least one weighting factor to determine a wear therefrom.

In some embodiments, the method is characterized in that a plurality of wear factors is determined.

In some embodiments, the method is characterized in that the wear factors are offset to form an overall factor and the overall factor is offset with the time period of the usage to form an overall wear.

In some embodiments, the method is characterized in that at least one wear factor is determined for each of individual components and/or component groups of the ventilator.

In some embodiments, the method is characterized in that the time period of the usage of the ventilator is offset with the respective wear factors of the components and/or component groups to determine the wear of the respective component and/or component group therefrom.

In some embodiments, the method is characterized in that an average wear factor is determined for each wear factor and a prediction with respect to the respective wear is made on the basis of the respective average wear factor.

In some embodiments, the method is characterized in that, on the basis of the determined wear and/or the prediction of the wear, an optimum maintenance point in time is determined and a corresponding message is generated.

In some embodiments, the method is characterized in that after a time period after which the maintenance point in time is exceeded, an alarm message is generated and if the maintenance still does not occur, the ventilator and/or specific functions of the ventilator are blocked until the maintenance has been carried out.

In some embodiments, the method is characterized in that after completed maintenance, the blocked ventilator or the blocked functions is/are unblocked again and/or the alarm message is deactivated.

It is to be pointed out that the features listed individually in the claims can be combined with one another in any technically reasonable manner and disclose further embodiments of the invention. The description additionally characterizes and specifies the invention in particular in conjunction with the figures.

It is furthermore is to be pointed out that a conjunction "and/or" used herein, standing between two features, and linking these features to one another is always to be interpreted so that in a first embodiment of the subject matter according to the invention only the first feature can be provided, in a second embodiment only the second feature can be provided, and in a third embodiment both the first and also the second feature can be provided.

A ventilator is to be understood as any device which assists a user or patient in the natural respiration, takes over the ventilation of the user or living being (e.g., patient and/or newborn and/or premature infant) and/or is used for respiratory therapy and/or influences the respiration of the user or the patient in another way. These include, for example, but not exclusively CPAP and BiLevel devices, narcosis or anesthesia machines, respiratory therapy devices, (clinical, home, or emergency) ventilators, high-flow treatment devices, and coughing machines. Ventilators can also be understood as diagnostic devices for ventilation. Diagnostic devices can be used in general here for detecting medical and/or respiration-related parameters of a living being. This also includes devices which can detect and optionally process medical parameters of patients in combination with the respiration or exclusively relating to the respiration.

If not expressly described otherwise, a patient interface can be understood as any peripheral device which is designed for the interaction of the measuring unit with a living being, in particular for treatment or diagnostic purposes. In particular, a patient interface can be understood as a mask of a ventilator or a mask connected to the ventilator. This mask can be a full face mask, thus enclosing the nose and mouth, or a nose mask, thus a mask only enclosing the nose. Tracheal tubes or cannulas and so-called nasal glasses can also be used as a mask or patient interface. In some cases, the patient interface can also be a simple mouthpiece, for example a tube, through which the living being at least exhales and/or inhales.

It is furthermore is to be pointed out that components and component groups are used synonymously with one another in the course of the description and claims. If not explicitly emphasized, a component is also always to be understood as a component group, thus a combination of multiple components to form a group. A component group can also be understood as a single component.

To determine the usage intensity of a ventilator, it is provided that the device according to the invention comprises at least one control unit and a usage clock. The duration of the usage of the ventilator is detected via the usage clock. The control unit is configured here such that the duration of the usage is offset with a wear factor to determine a wear therefrom.

It is provided, for example, that the control unit determines multiple wear factors. Depending on operating parameter and/or component and/or function used, for example, a separate wear factor can be determined. Separate wear factors are provided in particular for various components of the ventilator and/or component groups.

The control unit is also configured and designed, for example, to determine the number and/or duration of the charging cycles or the capacitance or the internal resistance of the accumulator or other indicators for the usage of the accumulator and to take them into consideration for the determination of at least one wear factor.

The separate wear factors are offset to form an overall factor via the control unit. It can be provided here that different wear factors are offset with different weightings to form the overall factor. The overall factor is used by the control unit to determine an overall wear for the ventilator via an offset with the duration of the usage. The overall wear can be representative here for a general condition of the ventilator. The overall wear can be provided so that it reflects a general status of the wear of the ventilator in a number and/or information. A user and/or caregiver is thus enabled, for example, to assess the condition of the ventilator on the basis of a simple number and/or information.

A simple offset of overall factor and duration of the usage can be carried out, for example, via a multiplication, so that the wear is indicated in the form of a duration. In some embodiments, it can be provided that further factors are introduced, for example, to generate a unitless parameter for the wear.

The overall factor can alternatively or additionally also represent an average, possibly weighted, of all individual wear factors and/or wears. It can be provided for this purpose that the wear factors are scaled, so that they are comparable to one another. For example, it can be provided that the wear is represented as a fraction and/or percentage, wherein 100% can correspond to complete wear and/or reaching a maintenance limit, thus a point in time at which the ventilator and/or the relevant component is to be maintained.

Alternatively or additionally, it can be provided that the overall wear represents the wear of the component, the wear of which is highest.

Together with the overall wear, the wear of the components having the highest and having the lowest wear can also always be displayed or output.

For individual components and/or component groups, determining separate wears can be provided. For this purpose, at least one wear factor is assigned to each of the components, which is offset with the duration of the wear to determine the wear. The wear of the individual components can be determined here independently of the overall wear.

Alternatively or additionally, it can be provided that the wear of the individual components is also incorporated into the overall wear. For example, the overall wear can be calculated proportionally by an offset of the overall factor with the duration of the wear and proportionally by an offset of the wear of individual components.

It is provided, for example, that different operating parameters of the ventilator can be included in the wear factors, for example, as subfactors. A different calculation basis can be provided here depending on the wear factor.

For example, it can be provided for some wear factors that depending on the value of the operating parameter, a chronological accumulation of a subfactor assigned to the value is used. If, for example, a value a of the subfactor 2 is assigned to a set and/or measured operating parameter and if this value a exists for 10 time units, the corresponding wear factor thus results in the value 20. It can be provided for all wear factors that a unit factor is provided in the calculation in each case, which makes the wear factor unit-free. If multiple subfactors are included in a wear factor, it can thus be provided, for example, that the subfactors are added together and/or multiplied with one another. Weighting of the subfactors can also be provided. In some embodiments, it can moreover be provided that operating parameters are calculated into various wear factors with different subfactors. It can thus be taken into consideration when various components, to which different wear factors are assigned, are affected in different ways by the same operating parameters with respect to the wear.

A calculation of the overall wear can be carried out, for example, according to $$GA=TG\cdot GF$$

wherein GA is the overall wear, TG is the duration of the usage of the ventilator, and GF is the overall factor. The overall factor GF is calculated, for example, via $$GF=\Sigma(AF_i\cdot G_i)$$

wherein $AF_i$ is the wear factor and G is the associated weighting factor. The individual wear factors $AF_i$ follow, for example, from $$AF_i=\Sigma BP_i$$

and/or $$AF_i=BP_i\cdot BP_2\cdot\ .\ .\ .\ \cdot BP_i$$

wherein BP denotes the respective subfactors which are assigned to specific operating parameters. In this case only the subfactors or operating parameters are also included in the calculation of the wear factors which are assigned to the respective wear factors.

In some embodiments, a calculation of the overall wear GA can also be carried out via $$GA=\Sigma(K_i\cdot G_i)$$

wherein K is the wear of individual components. The wear of individual components K can be produced, for example, on the basis of a sum of the wear factors linked to the respective component multiplied by the duration of the usage of the respective component.

An operating parameter can be, for example, the selected treatment mode. A distinction is made here, for example, between a CPAP and a BiLevel mode. Further treatment modes can also be taken into consideration. For example, invasive and noninvasive ventilation, servo ventilation (for example anti-cyclic), mouthpiece ventilation, nasal high-flow treatment, autoCPAP mode, generally automatic ventilation modes such as using autoEPAP (automatic expiratory, positive airway pressure), or target volume control are to be mentioned here. For example, a separate subfactor is provided for each treatment mode. The subfactor can take into consideration certain settings in a generalized manner for each treatment mode, for example. If a frequent change of the ventilation pressure is provided for a treatment mode, a higher subfactor can be provided for the treatment mode than for a treatment mode having fewer changes of the ventilation pressure. An increase of the subfactor which is assigned to a treatment mode can also take into consideration whether additional functions such as humidifying and/or heating of the respiratory gas is provided. In some embodiments, it is provided here that a preset subfactor is assigned to a treatment mode.

Another operating parameter can take into consideration, for example, the treatment pressures. For example, higher pressures represent a greater load for the ventilator and/or individual components. It can accordingly be provided that a higher treatment pressure also results in a higher subfactor or wear factor. In some embodiments, for example, it can also be taken into consideration that various components have different optimum load ranges with respect to the treatment pressure. It can accordingly be provided that the influence of the treatment pressure on the wear factor is accordingly taken into consideration differently depending on the component. The treatment pressure can be measured and recorded, for example, via a pressure sensor of the ventilator.

A further possible operating parameter can be settings with respect to a ramp between the inspiratory pressure level (IPAP) and the expiratory pressure level (EPAP). For example, the slope of the ramp can also be incorporated here. A greater slope can be accompanied, for example, by a greater factor than a comparatively flat ramp. It can be provided, for example, that the slope is incorporated as a subfactor for the wear factor of the turbine/the fan or the corresponding motor. A greater slope of the ramp means for the motor here that the speed has to be accelerated or decelerated more strongly, which results in a higher load and thus also faster wear of the motor. The operating parameter of the ramp can be used, for example, as a generalized factor here, which remains constant for the overall treatment time period for which the ramp is set. If the ventilator is configured to dynamically adapt the ramp in accordance with the respiration of the patient, the operating parameter ramp can thus also be calculated in as dynamic factor. A corresponding factor for the ramp is determined and calculated in proportionally for this purpose upon each change between EPAP and IPAP.

A measured leakage can also be included as an operating parameter in wear factors. A higher leakage can apply here, for example, as a higher factor, since a higher gas flow has to be generated due to a higher leakage in order to compensate for the leakage. The operating parameter of the leakage can optionally also be incorporated in the consideration of a respiratory gas humidifier, wherein a higher leakage simultaneously contributes to a higher wear of the respiratory gas humidifier, since a greater amount of respiratory gas has to be humidified per unit of time than in the case of a lower leakage.

The speed of the turbine or the fan can represent a further operating parameter. For example, a speed is specified and/or measured by the control unit. The speed of the turbine can in particular be incorporated into the wear factor which is assigned to the turbine and/or the motor of the turbine. In some embodiments, it is provided here that speed ranges are defined, wherein corresponding subfactors are assigned to each of the speed ranges.

Together with or independently of the speed, it can also be provided that speed changes are also incorporated as operating parameters in the wear factors. A frequent and/or larger change of the speed, for example, by acceleration or deceleration, can be assessed, for example, as a greater load and is incorporated with a greater factor into the wear or the wear factors.

The number of switching actions of valves can also be used as operating parameters to determine wear factors. For example, the device comprises a counter unit which detects the number of the switching actions provided. Alternatively or additionally, it can be provided that the time between two switching actions of the same valve is also incorporated. If the time between two switching actions falls below a specific threshold value, for example, an elevated influence in relation to two switching processes lying further apart can be calculated in for this purpose. The influence can also be calculated in an accumulating manner, for example. If multiple switching actions are registered, for example, between which the time falls below a threshold value, the influence or the subfactor thus increases more and more. It is thus taken into consideration that rapid switching actions in succession represent a greater load for the valve.

Additionally or alternatively, trigger settings can also be viewed as operating parameters. The sensitivity can play a role here, for example. A higher sensitivity can result in a higher rate of incorrect triggers, for example, thus situations in which the ventilator switches over between inspiration and expiration although such switching over is not necessary. As a result, for example, the patient breathes for a time period against the ventilator and thus exerts a higher load on the device. Since the same thing can also apply for an excessively low sensitivity of the trigger, it can be provided that the number of incorrect triggers, thus switching over at the wrong point in time and/or absent switching over, is also incorporated into the wear factors.

A measured respiratory gas flow can also be considered an operating parameter. A high respiratory gas flow can result in a higher wear factor here, for example. The respiratory rate of the patient is also taken into consideration as an operating parameter. It can be provided that the respiratory gas flow is averaged over a time period, for example, over an hour and/or a day. Among other things, the progress of the wear may be determined and/or at least estimated from the mean value. The change of the respiratory gas flow can also be used as an operating parameter, for example, each change individually and/or as a mean value or median over a time interval. Thus, for example, acceleration and/or deceleration procedures of the turbine or the fan may be incorporated via the change of the respiratory gas flow.

The accessories and peripheral devices used can also be calculated in as a further operating parameter in the wear factors. In some embodiments, the ventilator is optimized, for example, for operation with specific accessories such as masks, hoses, and/or humidifiers. Accessories deviating therefrom can cause faster wear of individual components, for example, and are possibly also subject themselves to higher wear. Accordingly, individual subfactors can be assigned with the accessories. In some embodiments, the ventilator is configured to automatically recognize connected accessories and/or at least to recognize whether or not an optimized accessory is connected. The ventilator can also be configured to recognize and/or measure specific properties of the connected accessory. For example, the ventilator can determine the resistance of the connected hose system and/or the connected patient interface. A higher measured resistance can be included here with a higher factor.

Inter alia, in conjunction with connected accessories, a pneumatic resistance can also be included as an operating parameter in the wear of various components. A higher pneumatic resistance represents, for example, a higher load for the turbine or the fan and can thus result in an increase of the respective wear factors.

Additionally or alternatively, it can be provided that the operation of connected respiratory gas humidifying and/or respiratory gas heating is also incorporated as an operating parameter in the wear factors. The measured and/or set humidity or temperature can play a role here, for example. For example, there can be an optimum temperature and/or humidity range, wherein a higher wear is to be expected in operation outside these ranges and the wear factors and/or subfactors are accordingly assessed higher.

In addition to the respiratory gas humidity and respiratory gas temperature, ambient conditions such as temperature, humidity, and/or air pressure can also be taken into consideration as operating parameters. Ideal ranges can also be defined here, for example, in which the subfactors or wear factors are accordingly assessed lower than in operation outside these ranges.

The air quality, such as the content of dust and/or other particles, can also be used as an operating parameter. A high dust content of the ambient air can contribute, for example, to the filters of the ventilator being filled or clogged faster. An increased dust content can also act on the bearings of the turbine, for example, due to an accumulation of dust particles on the bearing and/or in lubricants. The dust can also be deposited on and/or in various other components, for example, in foams which are used for sound insulation.

The number of patient changes and/or procedures for hygienic preparation can also be relevant operating parameters. Various types of hygienic preparation act differently on the wear here. It can be provided, for example, that the control unit recognizes automatically and/or semiautomatically which preparation method is used and possibly also recognizes the duration of the preparation. Alternatively or additionally, it can be provided that a user saves items of information and/or data on the hygienic preparation, for example, the type and duration of the preparation, in the ventilator. In some embodiments, the ventilator has a selection of preparation methods which can be selected by the user.

The use of various preset programs, for example, a day and night mode between which the user/patient can select, can also be incorporated as an operating parameter in the wear factors. A calculation of the ratio between the programs is conceivable here. It can also be provided that the usage duration or the wear is determined individually on the basis of the programs and then added up for each component to form an overall wear. For example, the wear of a component is then determined in that the wear from the individual programs, such as the day and night mode, are added up.

It can also be provided that a wear of a display is determined, inter alia, on the basis of the day and night mode. It is decisive here, for example, at which brightness the display is operated. The display brightness and/or the general usage of the display is typically turned down strongly for a night mode, so that a lesser load of the display results, thus a lower wear is to be recorded in the night mode.

It can alternatively or additionally also be provided that the oxygen feed and/or admixture is calculated in as an operating parameter in the wear factors. For example, this is also accompanied by whether oxygen admixing is activated or not and in which amount and over which time period oxygen is admixed. For example, a higher amount and/or longer duration is included with a higher subfactor in the wear factors.

Further operating parameters are to be found in the use of auxiliary functions such as hose heater, humidification, and/or convenience functions (autostart, starting ramp, stopping ramp, etc.). If, for example, a starting/stopping ramp is used, this can be considered with a reduction of the subfactor and/or the wear factor, since the ventilator passes slowly into the final operating state instead of a "sudden" start of the ventilation. An autostart function, in contrast, can have an increasing effect on the subfactor/wear factor, since possibly a basic activity of the ventilator is presumed here and/or various sensors have to be activated. The activation of a hose heater has an effect, for example, especially on the wear factor of the hose system, for example, an ideal temperature range can be provided for the hose system and operation outside this temperature range results in faster or higher wear, which is reflected in the wear factor.

The frequency of specific maneuvers such as a coughing aid and/or a cough by the patient can also be provided as an operating parameter. Such special maneuvers exert an additional load on the ventilator here, so that these can be accompanied, for example, by an increase of the wear factor.

The use of filters, for example, bacterial filters, are also provided as operating parameters in some embodiments, which are also included in the wear factors. For example, it can be provided that filters be calculated in with an influence reducing the wear factor, wherein the corresponding subfactor can be dependent on the wear of the filter itself. For example, the control unit can be configured to estimate and/or measure the loading of the filter and to increase the subfactor for the filter in the event of higher loading, for example, upon exceeding a threshold value. The loading of the filter can be determined, for example, via the flow and the pressure to be generated, which is related thereto, and/or the required speed of the turbine motor and/or a pneumatic resistance. In some embodiments, a higher loading of the filter causes a lower flow, which is compensated for in that a higher pressure has to be exerted to achieve the provided flow.

The usage time of additional sensors, e.g., CO2, SpO2, O2, FiO2, humidity, temperature can also be viewed as an operating parameter. For example, it can be provided that the usage time is used directly as a wear factor and/or also represents a wear directly for the sensors. The wear of a sensor can be dependent, for example, only on the usage time of this sensor. The wear of the sensor can thus also be incorporated directly, possibly in weighted form, into the overall wear. Alternatively or additionally, the number and/or duration of the uses of the FiO2 sensor can also be incorporated in the wear factor or factors.

A further operating parameter which can also be incorporated in the calculation or determination of the wear factors relates to the power supply. For example, the power consumption can be taken into consideration here. If a higher power consumption results in a higher load, for example, of the power supply unit and/or an accumulator, for example, the resulting wear factor can accordingly be higher. The control unit is configured and designed, for example, to determine the number and/or duration of the charging cycles or the capacitance or the internal resistance of the accumulator or other indicators for the usage of the accumulator and take them into consideration for the determination of at least one wear factor. Indicators for the usage of the accumulator are in particular those mentioned hereinafter: Alternatively or additionally, the number and/or duration of the charging cycles of the accumulator can also be incorporated in the wear factor or factors. It can also be provided that the point in time of the beginning of charging is also incorporated, for example, with regard to the state of charge of the accumulator. For example, the number of the charging cycles can also be weighted via the state of charge of the accumulator. A higher state of charge at the beginning of the charging can mean, for example, a higher wear factor, in particular for the accumulator, than a rather low state of charge. Alternatively or additionally, the capacity of the accumulator can also be incorporated into the wear factors. The capacity measurement is carried out here in consideration of the maximum permissible charging/discharging currents of the accumulator. In particular, the capacity during charging can also be determined for the determination of the wear factor.

Alternatively or additionally, the internal resistance of the accumulator can also be incorporated in the wear factors. The measurement of the internal resistance is carried out here in consideration of the maximum permissible charging/discharging currents of the accumulator. In particular, the internal resistance during the charging can also be determined for the determination of the wear factor. Alternatively or additionally, the calendar age of the accumulator can also be incorporated in the wear factors. Alternatively or additionally, the number of the charging cycles can also be counted and incorporated in the wear factor. Alternatively or additionally, the state of charge can also be determined at the beginning and at the end of the charging cycle, to determine how deeply the accumulator was discharged, how strongly it was recharged, and the result can be incorporated into the wear factor. Alternatively or additionally, the strength of the charging currents/discharging currents and/or the provided power can also be incorporated as a result in the wear factor.

The ambient conditions during usage procedures and charging procedures, such as the temperature or the ambient humidity, can also be determined and incorporated in the wear factor.

Alternatively or additionally, behavior during the present charging cycle can also be determined and incorporated into the wear factor, for example, as the internal resistance of the accumulator and/or heating behavior in dependence on the charging current and/or remaining accumulator capacity and/or current/voltage characteristic curve during the charging.

Alternatively or additionally, a relative change of properties of the accumulator from the new state can also be determined and incorporated into the wear factor, wherein the properties of the accumulator are determined in the new state and stored for this purpose.

Wear factors can also include, for example, the hardware version of individual components. For example, a newer hardware version can be optimized in operation and/or lower maintenance, due to which a lesser wear can be observed. Additionally or alternatively, it can also be considered that various hardware versions also have various operating ranges, thus ranges in which a lower wear is to be observed than outside these ranges.

In some embodiments, for example, the material of the components can also be taken into consideration. For example, it is possible to distinguish between long-lived, normal, and/or short-lived components. It can accordingly be provided, for example, that the materials of the components are also incorporated into the wear factors. In some embodiments, it can also be provided that the maximum wear and/or duration of the usage until the maintenance and/or replacement of the component is adapted accordingly. Short-lived components have to be subject to maintenance and/or replacement, for example, after a shorter usage time. The material of the components plays a role, for example, in the masks, hoses, sensors, accumulators, and/or fans/respiratory gas sources used.

The firmware version of the ventilator or individual components can also be reflected in the wear factors. Newer firmware can be optimized, for example, with respect to the control, so that a lower load of individual components or the ventilator can be implemented and accordingly a lower wear factor and/or subfactor can be estimated.

It can also be provided that the consumption of data volume, for example, for sending data via mobile wireless and/or Bluetooth and/or WLAN, is viewed as an operating parameter and/or is included in wear factors. For example, a specific data volume is provided per unit of time, for example, per month. If this provided data volume is consumed, for example, specific transfer channels and/or the transmission function in general can be blocked. A prediction can also be created via already consumed data volume as to whether the provided data volume is sufficient. If it is predicted that the provided data volume is not sufficient, for example, a message is output and/or the transmitted amount of data is reduced and/or the frequency of the data transfer is decreased. It can additionally be provided that a manual transmission function is deactivated. It can also be provided that a safety data volume is kept in reserve, so that a transmission of alarms and/or emergency messages nonetheless remains possible.

If a maximum utilization of the data volume is reached, thus the available data volume is consumed, an automatic type of the maintenance or replacement can thus be carried out here. A maintenance or replacement provides here, for example, that in the case of prepaid data volumes, thus a data volume which is booked beforehand, the data volume is loaded. For example, an additional fee becomes due for this purpose, which is added to a total fee. If a rate data volume is provided, it can be provided that the control unit carries out an automatic change of the rate, for example, to a rate having higher available data volumes. In some embodiments, it can be provided here that the change has to be confirmed by a user and/or caregiver. In some embodiments, it can also be provided that a contingent of data volume is provided for a plurality of ventilators. Upon a consumption of the provided data volume of one ventilator, the remaining data volume from the overall contingent can then be redistributed or additional data volume can be released, for example, by subtracting data volume from devices having lower consumption of data volume.

A further operating parameter can also be the number or frequency of the maintenance of the ventilator and/or individual components. For example, frequent opening of the ventilator can result in a higher load of the housing. Installing and removing individual components can also have an effect on the wear of the ventilator.

The wear can be determined completely for the ventilator, for example, and/or separately for individual components such as turbine, humidifier, water chamber, air filter, hose, patient interface, foams, electronics, power supply unit, sensors, measuring cells, etc.

It can also be provided in this case that one or more wear factors are assigned to each component. The wear factors determine here, for example, how strongly various operating parameters act on the respective component. It can also be considered here that the same operating parameters are calculated, for example, weighted, differently into different wear factors. Alternatively or additionally, the operating parameters can be incorporated with different subfactors into the wear factors.

Additionally, it can be provided that a prediction with respect to the wear of individual components and/or the ventilator is made on the basis of the wear and/or the wear factors. For example, the wear is extrapolated in this case. The progress of the wear can also be incorporated into the calculation of the prediction, for example. The more recent progress over time of the wear is weighted more strongly than that lying further back in time, for example. In some embodiments, the wear factors and/or the overall factor are additionally or alternatively used as the basis of the prediction.

On the basis of the prediction of the wear, for example, a duration can be calculated until a maintenance and/or replacement of the component and/or the ventilator becomes due. An optimum maintenance point in time can be determined via the prediction, for example.

Alternatively or additionally, it can also be provided that the actual wear can be measured via various parameters. For example, it is conceivable that the vibrations are detected which the turbine/the fan generates, wherein the condition of the bearings can be concluded, for example. The heat output of individual components, thus how strongly the components heat up during operation and possibly also cool down again after operation, can thus also be detected as parameters, from which inferences can be drawn about the wear. Stronger heating with uniform performance of a component can be an indication of progressing wear, for example. A pneumatic resistance can also be used to detect, for example, the soiling of individual components, in particular filters. The agility of the ventilator, thus, for example, how quickly switching over between various pressures and/or flows takes place, can also give indications of the wear of individual components, for example, valves and/or the respiratory gas source.

It can also be provided that the control unit is configured and designed to determine a maintenance point in time on the basis of the individual types of wear, wherein the largest possible number of components falls in a maintenance window. For example, in particular for noncritical components, the maintenance point in time can be delayed so that other components also come into a maintenance window. It can be provided here that a specific critical wear is not exceeded. This critical wear triggers, for example, an immediate maintenance request.

Exceeding a threshold value for the overall wear and/or the wear of one single and/or multiple components can provide one or more actions.

One action can be, for example, the generation of a communication. The communication can be generated, for example, by the ventilator. In some embodiments, it is provided that the communication is transmitted to a distant remote station, for example, software, a cloud, an app, a server, and/or other external display devices. The communication can then, for example, notify a caregiver of required maintenance and/or inform about the wear status of the ventilator.

In some embodiments, it is provided that the data for determining the wear and/or the wear factors are transmitted to a distant remote station and the distant remote station calculates the wear. Moreover, it can be provided that the distant remote station generates a communication with respect to the wear, for example, a notice of a required maintenance and/or about the wear status of the ventilator. The communication can be transmitted to the ventilator and possibly displayed there. It can also be provided that a message is sent from the communication, for example, via postal mail/letter and/or email. A display of the communication via an app can also be provided in some embodiments.

The communication can also contain an item of information and/or data about the duration in which a maintenance and/or replacement of components and/or the ventilator will become necessary, for example, based on a prediction.

For some embodiments, it is provided that the communication contains notifications as to when and/or that a maintenance is necessary. The notifications can be given, for example, in various escalation levels and can possibly be linked to further actions. If, for example, a maintenance is provided in a future time period, for example, based on a prediction, a message can be displayed on the ventilator, which requests a maintenance. It can be provided here that the user has to confirm the message.

If the point in time is reached at which the wear reaches and/or exceeds a threshold value, upon which a maintenance is necessary, a next escalation level can be reached. In this level, the user can be notified, for example, upon each further use and/or in periodic time intervals, which become shorter, that a maintenance and/or component replacement is necessary. Before the use of the ventilator, it can be provided, for example, that this message has to be confirmed by the user. It can also be provided, for example, that in addition a referral is offered and/or contact information is shown, via which further steps of the maintenance can be explained or agreed upon. For example, a referral can be made to an appointment booking for a maintenance. In some embodiments, upon successful appointment booking, feedback is given to the ventilator which at least temporarily deactivates the notifications for maintenance. In the case of an appointment booking, it can also be provided, for example, that the ventilator generates a reminder which notifies the user of an upcoming maintenance appointment. Alternatively or additionally, it can be provided that a corresponding message takes place via postal mail and/or email and/or app. It can be provided, for example, that an appointment confirmation is sent via postal mail and/or an appointment reminder is transmitted via email and/or app to the user of the ventilator. In some embodiments, the transmission path is made dependent on which paths are available to the respective user. If, for example, an app is not used and/or an email address is not saved, it can be provided that communications or messages are transmitted exclusively via postal mail and/or the ventilator.

Alternatively or additionally, it can be provided that a message is simultaneously displayed via an external remote station, for example, for a caregiver, that the ventilator and/or a component has to be maintained and/or replaced. If steps for maintenance and/or replacement are initiated, for example, it can be provided that the notifications for maintenance are at least temporarily deactivated via feedback to the ventilator.

A further escalation level can be reached, for example, when a specific time period is exceeded after the notification of required maintenance has been generated. It can be provided, for example, that the ventilator generates and/or displays a notification or a message which requests immediate maintenance and cannot be hidden. In some embodiments, it can also be provided that the ventilator and/or individual functions are blocked when the maintenance does not occur over a time period. The blocking of the ventilator or individual functions can also be provided as a further escalation level.

Alternatively or additionally, it can be provided that certain components enter a safe mode. In the safe mode, the relevant components are then operated, for example, with lower output. For example, the heating output of the respiratory gas humidifier is reduced, which results in a longer service life at a lower output. The turbine/the fan can also be operated at a lower output, for example. The service life, therefore also the wear, can thus be extended. For example, it can be provided that the output is reduced step-by-step if maintenance does not occur. It can also be provided here that in specific situations the safe mode is suspended to be able to retrieve a high output if needed. This relates in particular to situations in which the safety and/or health of the patient can be impaired. If the patient falls into a respiratory situation or respiratory problem, for example, which requires a high output of specific components, these can be taken out of the safe mode to remedy the respiratory problems.

The safe mode can also apply for linked components, for example. If the accumulator needs a maintenance and is transferred into the safe mode, for example, together with this, for example, the output of the respiratory gas source can also be reduced in order to additionally protect the accumulator.

If the treatment of the patient should become impossible due to a lack of maintenance of the ventilator and/or individual components, it can be provided that an alarm is generated. This alarm can be output on the ventilator, for example, to inform the patient. An alarm message can also be provided at a distant remote station, for example, at the caregiver and/or provider. In some embodiments, it can be provided that the shipping of a replacement device accompanies the alarm message.

The ventilator or the control unit can also be configured and designed, for example, to detect a maintenance and/or the replacement of components and to thereupon automatically reset the wear. For example, the wear of the maintained and/or replaced components can be reset. If the ventilator was blocked due to a lack of maintenance, it can be provided that the ventilator is automatically unblocked by the performed maintenance. Alternatively or additionally, it can be provided that after maintenance is performed, the ventilator has to be manually unblocked, for example, by a caregiver.

In some embodiments, specific maintenance work can be carried out as self-service by the user or the patient themselves. If a wear which provides a maintenance and/or a replacement is reached, for example, for components which can be maintained and/or replaced by the patient, in addition to the message that a maintenance is provided, an item of information can also be displayed which shows the maintenance steps. In some embodiments, it is also provided that for the maintenance of components which the patient can carry out independently, the required parts, for example, replacement components, are automatically shipped to the patient, as soon as the maintenance is recognized as necessary. The ventilator can be configured, for example, to detect completed maintenance and to reset the wear. Any notifications and requests for maintenance can then also be automatically deactivated by the ventilator.

Alternatively or additionally, upon reaching the threshold value for maintenance/for replacement, shipping of maintenance material and/or replacement components to a previously defined location can automatically be initiated. For example, the shipping of a replacement component is automatically initiated so that it arrives at the location of the maintenance together with a maintenance appointment.

For specific components, it can also be provided that in addition to a wear, a counter is also configured which represents the status until the replacement of the component. For example, the counter can also be decremented by a maintenance, and thus reset of the wear of the components, wherein the counter can only be completely reset by replacement. This relates, for example, to components, the service life of which can be extended by regular maintenance.

After maintenance is performed, in some embodiments the maintenance point in time is saved in the ventilator. In some embodiments, the control unit is configured and designed to generate an additional or alternative estimation or prediction with respect to future maintenance points in time on the basis of the maintenance points in time.

In some embodiments, the wear factors and/or the subfactors are adapted via an artificial intelligence. It can be provided for this purpose that the effectiveness, etc. of a component is checked and/or recorded again and again. Via the artificial intelligence, for example, the wear status is compared to the output of the respective component, wherein the wear factor is corrected accordingly if needed. If the turbine motor wears out faster, for example, than predicted via the wear factor, the artificial intelligence can adapt the wear factor of the turbine motor or the incorporated subfactors to make a more accurate prediction in the further course of things. The wear of the turbine motor can be recognized, for example, in that more energy is required for the same speed.

For some embodiments, it is provided that a fee is determined on the basis of the wear. For example, the control unit generates a periodic report which contains the wear and/or a fee based on the wear. In some embodiments, this report can be transmitted automatically as an invoice to a predefined receiver. It is provided, for example, that a total fee per time interval, for example, per week/month/quarter/year is calculated from a base fee and a fee based on the determined wear, for example, a wear fee, of individual components and/or the overall wear. For example, a sum results total fee per time interval=base fee+(usage time in the time interval*wear factor)*fee factor, wherein the product of usage time and wear factor is calculated individually per component. It can also be provided that a weighting factor is additionally incorporated. This weighting factor can also, for example, incorporate to what extent the respective wear is dependent on the patient and/or treatment and to what extent an unavoidable wear occurs. If the ventilator is not used in a time interval, for example, only the base fee is thus due for this time interval.

It is also provided that the wear fee is automatically adapted to the wear. In some embodiments, it can also be provided that a mean value, median, and/or trend of the wear fees is determined and used as the basis for future time intervals, for example, as an advance payment.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
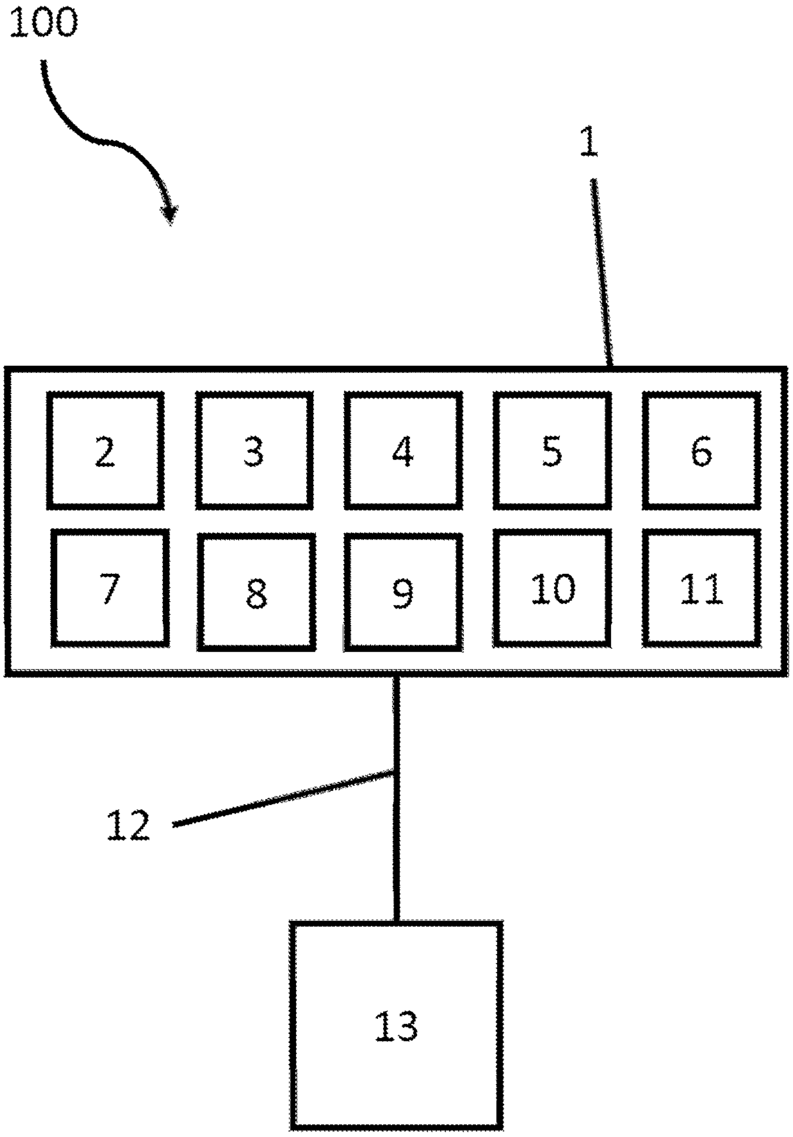
FIG. 1 shows an exemplary embodiment of a device for determining the usage intensity of a ventilator.

The ventilator 1 shown in FIG. 1 comprises by way of example a control unit 2, a usage clock 3, a sensor unit 4, a respiratory gas source 5, a recognition unit 6, an input unit 7, a display unit 8, an interface 9, a humidifier 10, and an oxygen source 11. A patient interface 14 is connected to the ventilator 1 via a hose system 13.

The usage clock 3 is configured and designed such that it can detect the duration of the usage of the ventilator 1. In some embodiments, the usage clock 3 is also designed to detect a separate duration for the usage of individual components and/or functions of the ventilator 1.

In some embodiments, the usage clock 3 is configured and designed such that the duration of the usage is only detected during a time interval or a time unit, for example, per day, and then transmitted, for example, to a distant remote station, which then adds up the duration of the usage over multiple time units/time intervals. It can also be provided here that exclusively or additionally the duration of the usage of individual components is detected.

The control unit 2 is configured and designed to determine the wear of individual components and/or the entire ventilator 1. The control unit offsets for this purpose at least one wear factor with the duration of the usage detected by the usage clock 3. The control unit 2 is moreover configured and designed to determine wear factors. The wear factors are determined via the control unit 2, for example, on the basis of various operating parameters. It can be provided that separate wear factors are assigned to individual components, also to determine separate wears of the respective component. Multiple wear factors can be offset or combined, for example, to form an overall factor, which is used to determine an overall wear for the ventilator 1. If only one wear factor is determined, this can thus correspond to the overall factor. In some embodiments, only one wear is accordingly also determined for the ventilator 1, wherein this wear then represents the overall wear, for example.

Operating parameters which form the basis of the wear factors can be, for example: firmware version; hardware version; treatment mode; treatment pressures; IPAP/EPAP ramp; leakage; speed of the turbine/fan; speed changes of the turbine; braking actions of the turbine; switching actions of valves; trigger settings; respiratory flow; respiratory rate; mask used; hose system used; humidifier; ambient temperature; ambient humidity; number of the hygienic preparations; day or night mode; oxygen injection; duration and/or amount of the oxygen admixture; use of auxiliary functions such as hose heating and/or respiratory gas humidifying; frequency of ventilation maneuvers; usage of additional sensors; status and/or source of the power supply; point in time of the last maintenance. The control unit 2 is configured to register or detect the operating parameters and to incorporate or offset them in wear factors. In some embodiments, individual components detect the operating parameters and transmit them to the control unit 2, which is configured to incorporate or offset the transmitted operating parameters in the respective wear factors.

In some embodiments, the device 100 comprises at least one storage unit (not shown), which is configured to store operating parameters, wear factors, wears, and/or durations of the usage and provide them for retrieval. For example, the operating parameters determined by individual components are stored in the storage unit, so that the control unit 2 can have access thereto and can retrieve the required data/values/items of information of the operating parameters.

It is provided that at least one operating parameter is incorporated by the control unit 2 in a wear factor. It can moreover be provided that different wear factors also take into consideration different operating parameters and/or the operating parameters are weighted differently.

The sensor unit 4 is configured and designed to detect and possibly evaluate pressures, flows, temperatures, and/or humidity. For example, the sensor unit is connected for this purpose to sensors which can be arranged in the ventilator 1 and/or are externally connected to the ventilator 1. For example, the sensor unit 4 is configured and designed to determine properties such as a respiratory flow, a breathing volume, a respiratory rate, phases of the respiration (at least inspiration and expiration) from a respiratory gas pressure and/or respiratory gas flow. The values and data detected by the sensor unit can be incorporated, for example, as operating parameters in wear factors or can be used as the basis of the determination of operating parameters. In some embodiments, the sensor unit 4 is also designed and configured to detect ambient temperatures and/or the ambient pressure.

The controllable respiratory gas source 5 is configured and designed to convey respiratory gas to and/or from a patient. For example, the respiratory gas source 5 can be designed as a fan. The fan comprises, for example, a turbine having turbine motor and turbine wheel. For example, the fan is configured and designed to detect a speed of the motor or the turbine wheel. The detected speed can be incorporated as an operating parameter in wear factors and for this purpose can be transmitted directly to the control unit 2 and/or (temporarily) stored in the storage unit.

In some embodiments, the control unit 2 is configured to actuate the fan, for example, to generate a predetermined pressure and/or flow. In some embodiments, a speed of the motor is specified for this purpose. It can also be provided that the control unit 2 specifies a pressure and/or flow and actuates the fan such that this pressure and/or flow is reached. It can also be provided that the control unit 2 and/or the fan and/or a recognition unit 6 determines the energy input to the motor or the fan. For example, an operating parameter and/or a wear factor can be determined on the basis of the energy input in relation to the achieved speed of the motor and/or the achieved pressure or flow.

Furthermore, it can be provided that a relationship between achieved pressure or flow and the speed of the motor is also incorporated or calculated in operating parameters or wear factors.

In some embodiments, the respiratory gas source 5 is alternatively or additionally embodied as a pressurized gas fitting, which is connected to an external pressurized gas source. For example, the respiratory gas flow and respiratory gas pressure can be regulated via valves. It can be provided that the control unit 2 and/or a counter unit records a number of valve switching actions and bases operating parameters for wear factors thereon. In some embodiments, it can be provided that in addition to the number of the switching actions, a time between the switching actions is also registered. Particularly fast switching actions in which the time between the switching actions falls below a threshold value can be included, for example, with a higher factor in the wear factors.

The recognition unit 6 is designed, for example, to detect various operating parameters which can also be incorporated in the wear factors. For example, it can be provided that the recognition unit 6 is configured to recognize connected accessories and/or components. It can be provided, for example, that some components transmit a type designation, serial number, and/or version information to the recognition unit 6, wherein the recognition unit 6 recognizes the component on the basis of these items of information. It can be provided for this purpose that the components are electrically connected for this purpose to a main board or a main printed circuit board and provide the corresponding items of information for retrieval. It can be provided that the recognition unit 6 and/or the control unit 2 adapts the wear factors on the basis of the recognized component, for example, with incorporation of an item of version information.

In some embodiments, the control unit 2, for example, in combination with the recognition unit 6, is designed to automatically detect a performed maintenance of the ventilator 1 and/or individual components. This can be carried out, for example, on the basis of the change of various operating parameters. If the motor of the turbine was maintained, for example, the control unit 2 can establish, for example, that after the maintenance a lower energy input is necessary for the same output and can thereupon conclude a maintenance of the motor. In the case of a filter, a lower gas pressure can already be sufficient, for example, to generate the same flow as before the maintenance. The control unit 2 can also conclude a replacement or the maintenance of the filter here.

Because the recognition unit 6 and/or the control unit 2 recognize the installed components, it can also be provided that a replacement of various components is recognized. If, for example, a maintenance and/or a replacement of a component is necessary, for example, due to the determined wear, the control unit 2 can establish whether the maintenance or the replacement was carried out.

Additionally or alternatively, the recognition unit 6 is configured and designed to detect operating parameters such as energy consumption, device output, energy source, and/or critical faults. Critical faults can be, for example, the failure of various components and/or functions. Intermittent overloads—for example of the respiratory gas source—can also be detected by the recognition unit 6. The recognition unit 6 can also be configured to measure and detect temperatures, for example, an operating temperature of the ventilator and/or individual components. It can thus be established, for example, whether individual components and/or the entire ventilator 1 are subjected to an elevated temperature.

The recognition unit 6 is furthermore configured to recognize peripheral devices/accessories such as a connected patient interface, a hose system, and/or a connected humidifier. Furthermore, it can be provided that the recognition unit 6 also recognizes which patient interface and/or hose system and/or humidifier it is. Such a recognition can be implemented, for example, via RFID chips in the components, which can be automatically detected by the recognition unit 6. It can also be provided that items of information on type, version, etc. of the accessory are transmitted to the recognition unit 6 and/or the control unit 2 automatically via an interface upon connection and a recognition of the accessory is thus possible. The control unit 2 can then optionally also detect items of information on resistance, heat output, etc. via the recognized accessory.

In some embodiments, it can be provided that if the recognition unit 6 or the control unit 2 does not recognize the connected accessory, it can at least be established via pressure and flow tests whether an accessory is connected at all.

The input unit 7 is configured so that data, items of information, and/or values can be input into the ventilator 1. For example, messages, notifications, warnings, etc. can be confirmed via the input unit 7. It can also be provided in some embodiments that a performed maintenance is confirmed and/or detected via the input unit 7. The input unit 7 is moreover configured so that specifications on the respiratory therapy can be made. For example, a pressure, flow, treatment mode, etc. can thus be defined via the input unit 7. The input unit 7 can be designed, for example, as a keyboard and/or further operating elements such as buttons and rotary controllers.

Via the display unit 8, for example, designed as a display, various data, items of information, values, messages, notifications, and/or alarms can be output at the ventilator 1. A display can take place graphically and/or alphanumerically, for example. Messages and notifications can include, inter alia, items of information on the wear of the ventilator and/or individual components. For example, it is possible to inform about an upcoming maintenance. Critical messages can also be displayed, for example, upon exceeding a maintenance time period or maintenance point in time.

It can also be provided that the display unit 8 and the input unit 7 are alternatively or additionally designed as a common information and operating interface, for example, as a touch-sensitive display screen (touchscreen).

It is provided that a transmission of messages and/or notifications, in particular on the status of the ventilator 1, to distant remote stations is enabled via the interface 9. The status of the ventilator 1 can comprise here, inter alia, an overall wear and/or the wear of individual components. Moreover, it can be provided that a message is transmitted via the interface 9 which triggers the shipping of materials required for maintenance and/or replacement components to a predefined address. The triggering can take place automatically, for example, as soon as a maintenance point in time is reached. In some embodiments, the shipping is triggered automatically when a maintenance appointment, for example, as a consequence of a required maintenance, is created via the ventilator 1.

The humidifier 10 is configured and designed, for example, to humidify and/or heat the respiratory gas. For example, the humidifier 10 has a water chamber having a heating element. Inter alia, the humidity of the respiratory gas can be set via the humidifier 10. In some embodiments, the control unit 2 and/or the recognition unit 6 is configured to recognize which humidifier it is. It can also be provided that it is possible to measure the water temperature and/or the respiratory gas temperature. For example, the humidifier 10 has corresponding temperature sensors for this purpose. The temperature of the water and/or the respiratory gas can be incorporated, for example, as an operating parameter in the wear parameters. It can furthermore be provided that the respiratory gas humidity which is measured and/or to be achieved is also used as an operating parameter. In some embodiments, it can be provided that the usage clock 3 detects a duration of the use of the humidifier 10. For example, a wear for the humidifier 10 can be determined via the duration of the use of the humidifier 10 together with a corresponding wear factor for the humidifier 10.

The optional oxygen admixing unit 11 is used for admixing oxygen to the respiratory gas. The oxygen admixing unit 11 can be connected, for example, to an external oxygen source. For example, the amount and duration of the oxygen admixing can be set via the oxygen admixing unit 11.

The patient interface 13 is connected to the ventilator 1 via the hose system 12. It can be provided that the recognition unit 6 and/or the control unit 2 automatically recognizes the hose system 12, for example, on the basis of an RFID chip or via a terminal, via which the hose system transmits items of information on type, etc. In some embodiments, the hose system 12 comprises a hose heater. The duration of the use and temperature of the hose heater can be calculated in here as an operating parameter by the control unit 2 in wear factors and/or wears.

Together with the hose system 12, the patient interface 13 can also be automatically recognized by the ventilator 1. For example, the patient interface 13 has an electrical contact via which items of information on the patient interface 13 are transmitted to the ventilator 1.

The control unit 2 can be configured and designed in some embodiments to make a prediction with respect to the wear via the progression of the wear and/or the wear factors. In some embodiments, it can be provided that the control unit 2 can also generate a prediction with respect to a maintenance appointment. In some embodiments, the control unit 2 is configured to incorporate more recent wear factors more strongly in a prediction than older ones and/or to take into consideration the more recent progression of the wear more strongly.

Figure 2:
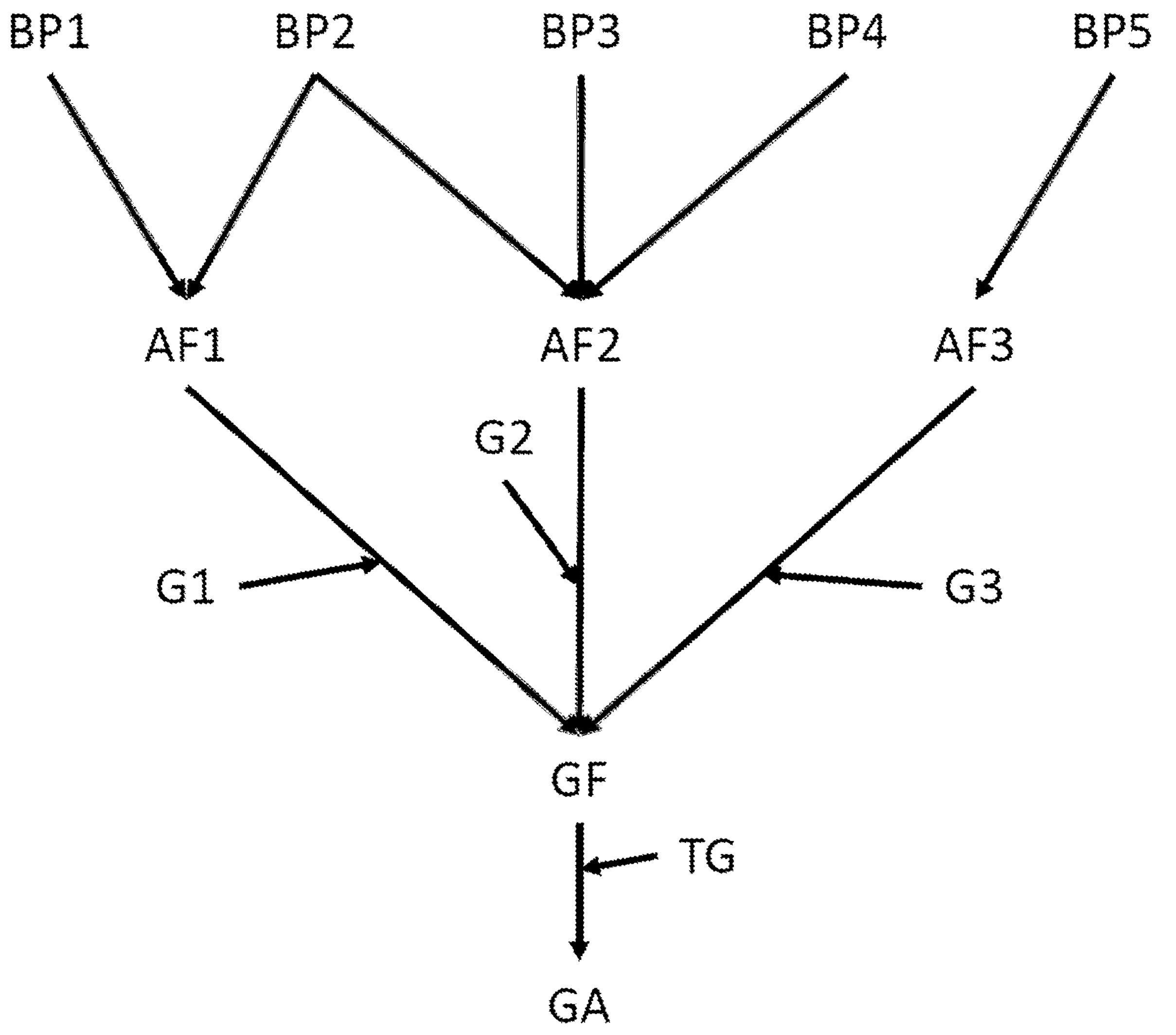
FIG. 2 and FIG. 3 show by way of example the determination of the wear factors of the ventilator and the overall factor in a greatly simplified manner.

FIG. 2 shows by way of example and in greatly simplified form how the wear factors AF1, AF2, AF3 are determined from the operating parameters or the associated subfactors BP1, BP2, BP3, BP4, BP5 and how the wear factors AF1, AF2, AF3 are included in the overall factor GF.

The operating parameter of the respiratory gas flow is represented, for example, via the subfactor BP1. The operating parameter of the selected treatment mode is represented, for example, via the subfactor BP2. The operating parameter of the speed of the turbine is represented, for example, via the subfactor BP3. The operating parameter of the respiratory gas pressure to be achieved is represented, for example, via the subfactor BP4. The operating parameter of the pneumatic resistance is represented, for example, via the subfactor BP5.

For example, the subfactors BP1 and BP2 are included in the wear factor AF1. An offset can be carried out, for example, via a multiplication of BP1 and BP2. The wear factor AF2 is based, for example, on a combination of the treatment mode BP2, the speed of the turbine BP3, and the respiratory gas pressure BP4. The subfactors BP2, BP3 and BP4 can be combined, for example, via a summation to form the wear factor AF2. The wear factor AF3 is only dependent, for example, on the pneumatic resistance BP5.

Via the weighting factors G1, G2, G3, the wear factors AF1, AF2, AF3 are offset to form the overall factor GF. The overall factor GF represents a wear factor for the entire ventilator. Via an offset, for example, a multiplication, of the overall factor GF with the duration of the usage TG of the ventilator, the overall wear GA is determined.

Figure 3:
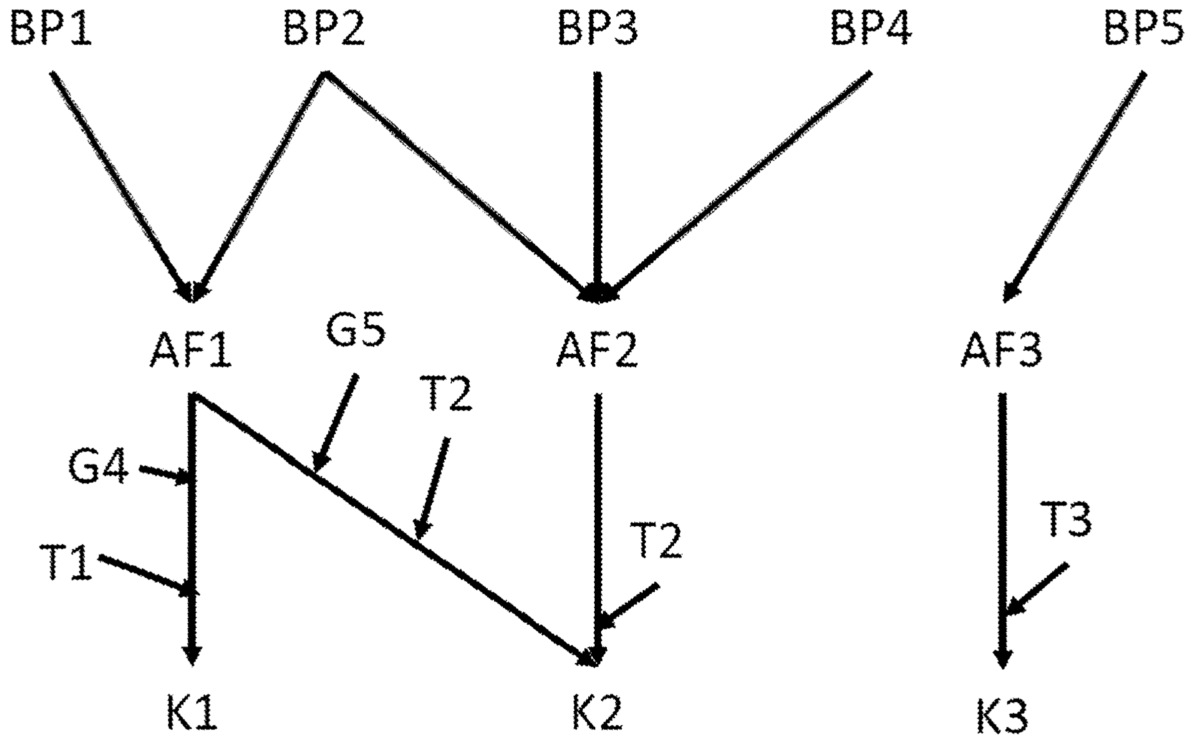

FIG. 3 shows by way of example the determination of the wear K1, K2, K3 of individual components. The wear factors AF1, AF2, AF3 are determined as described above under FIG. 2. The wear K1 represents, for example, the wear of a connected respiratory gas humidifier. To determine the wear K1 of the respiratory gas humidifier, for example, the wear factor AF1, which also incorporates the respiratory gas flow and the selected treatment mode, is offset with a weighting factor G4 and a duration T1 of the usage. The duration T1 can be, for example, a usage duration of the respiratory gas humidifier.

The wear K2 is, for example, the wear of the respiratory gas source. The wear K2 of the respiratory gas source is determined, for example, via the wear factors AF1 and AF2. The wear factor is included, for example, without weighting factor only via the duration T2 of the usage of the respiratory gas source in the wear K2 of the respiratory gas source. The wear factor AF1, in contrast, is calculated in via a weighting factor G5.

The wear K3 is, for example, the wear of a filter installed in the ventilator. The wear K3 of the filter is determined directly via the wear factor AF3 and the duration T3 of the usage of the filter.

LIST OF REFERENCE SIGNS

1 ventilator
2 control unit
3 usage clock
4 sensor unit
5 respiratory gas source
6 recognition unit
7 input unit
8 output unit
9 interface
10 humidifier
11 oxygen admixing unit
12 hose system
13 patient interface
AF1 wear factor 1
AF2 wear factor 2
AF3 wear factor 3
BP1 subfactor of operating parameter 1
BP2 subfactor of operating parameter 2
BP3 subfactor of operating parameter 3
BP4 subfactor of operating parameter 4
BP5 subfactor of operating parameter 5
G1 weighting factor 1
G2 weighting factor 2
G3 weighting factor 3
G4 weighting factor 4
G5 weighting factor 5
GA overall wear
GF overall factor
K1 wear of component 1
K2 wear of component 2
K3 wear of component 3
T1 duration of wear factor 1
T2 duration of wear factor 2
T3 duration of wear factor 3
TG duration of the usage

What is claimed is:

1. A device for determining a usage intensity of a ventilator, wherein the device comprises at least one control unit and a usage clock that is designed and configured to measure a duration of a usage of the ventilator, the at least one control unit being configured and designed to determine a plurality of wear factors by using various operating parameters of the ventilator, combine the plurality of wear factors to form an overall factor, determine an overall wear of the ventilator by combining the overall factor with the duration of the usage, determine an optimum maintenance point in time on the basis of a determined wear and/or a prediction of the wear and generate a corresponding message, generate an alarm message after a time period after a maintenance point in time is exceeded and if maintenance still does not occur, block the ventilator and/or specific functions of the ventilator until the maintenance has been carried out, and deblock the ventilator and/or specific functions of the ventilator and deactivate the alarm after the maintenance has been carried out.

2. The device of claim 1, wherein the at least one control unit is configured and designed to generate a message, which contains at least one notification of a maintenance, on the basis of a determined wear and/or a prediction of the wear.

* * * * *